(12) United States Patent
Graf et al.

(10) Patent No.: US 10,247,696 B2
(45) Date of Patent: Apr. 2, 2019

(54) METHOD FOR OPERATING A CHEMICALLY SENSITIVE FIELD-EFFECT TRANSISTOR

(71) Applicant: Robert Bosch GmbH, Stuttgart (DE)

(72) Inventors: Juergen Graf, Stuttgart (DE); Francisco Hernandez Guillen, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 321 days.

(21) Appl. No.: 15/029,349

(22) PCT Filed: Sep. 26, 2014

(86) PCT No.: PCT/EP2014/070665
§ 371 (c)(1),
(2) Date: Apr. 14, 2016

(87) PCT Pub. No.: WO2015/055403
PCT Pub. Date: Apr. 23, 2015

(65) Prior Publication Data
US 2016/0223489 A1    Aug. 4, 2016

(30) Foreign Application Priority Data

Oct. 15, 2013 (DE) .......... 10 2013 220 848

(51) Int. Cl.
*G01N 27/414* (2006.01)

(52) U.S. Cl.
CPC ....... *G01N 27/4141* (2013.01); *G01N 27/414* (2013.01)

(58) Field of Classification Search
CPC .................... G01N 27/414–27/4148
See application file for complete search history.

(56) References Cited

U.S. PATENT DOCUMENTS

2005/0230245 A1    10/2005    Morgenshtein et al.

FOREIGN PATENT DOCUMENTS

| CN | 1946836 A | 4/2007 |
|---|---|---|
| CN | 102203282 A | 9/2011 |
| JP | 2001-508880 A | 7/2001 |
| JP | 2002-98667 A | 4/2002 |
| WO | 2008/147497 A2 | 12/2008 |

OTHER PUBLICATIONS

Helbing et al., "Sensing NO2 with individual suspended single-walled carbon nanotubes," Sensors and Actuators B 132 (2008) 491-497 (Year: 2008).*
Estrada et al., "Reduction of hysteresis for carbon nanotube mobility measurements using pulsed characterization," Nanotechnology 21 (2010) 085702 (7 pp) (Year: 2010).*

(Continued)

*Primary Examiner* — Alexander S Noguerola
(74) *Attorney, Agent, or Firm* — Maginot, Moore & Beck LLP

(57) ABSTRACT

The disclosure relates to a method for operating a chemically sensitive field-effect transistor, characterized in that the field effect transistor is operated with electrical pulses, the time interval between said pulses being selected to be greater than the duration of each individual electrical pulse.

7 Claims, 2 Drawing Sheets

(56) References Cited

OTHER PUBLICATIONS

Lee et al., "Stability in OTFT gas sensors," Mater. Res. Soc. Symp. Proc. vol. 871E 2005 Materials Research Society pp. 11/5/1-11.5.6 (Year: 2005).*

International Search Report corresponding to PCT Application No. PCT/EP2014/070665, dated Nov. 24, 2014 (German and English language document) (7 pages).

Mori, Tomohiko, et al., Improving Baseline Stability of Gas Sensors based on Organic Field-Effect Transistors by Monitoring Carrier Mobility; 2011 IEEE Sensors Proceedings: Limerick, Ireland Oct. 28-31, 2011, IEEE, Piscataway, NJ, pp. 1002-1005, XP032093130.

Mescher, Marleen, et al., Pulsed Method for Characterizing Aqueous Media Using Nanowire Field Effect Transistors; IEEE Transactions on Electron Devices, IEEE Service Center, Piscataway, NJ, vol. 58, No. 7, May 19, 2011, pp. 1886-1891, XP011367835.

Yang, Richard, et al., Ultralow Drift in Organic Thin-Film Transistor Chemical Sensors by Pulsed Gating, Journal of Applied Physics, American Institute of Physics, US, vol. 102, No. 3, Aug. 15, 2007, pp. 34515-1-34515-7, XP012101454.

* cited by examiner

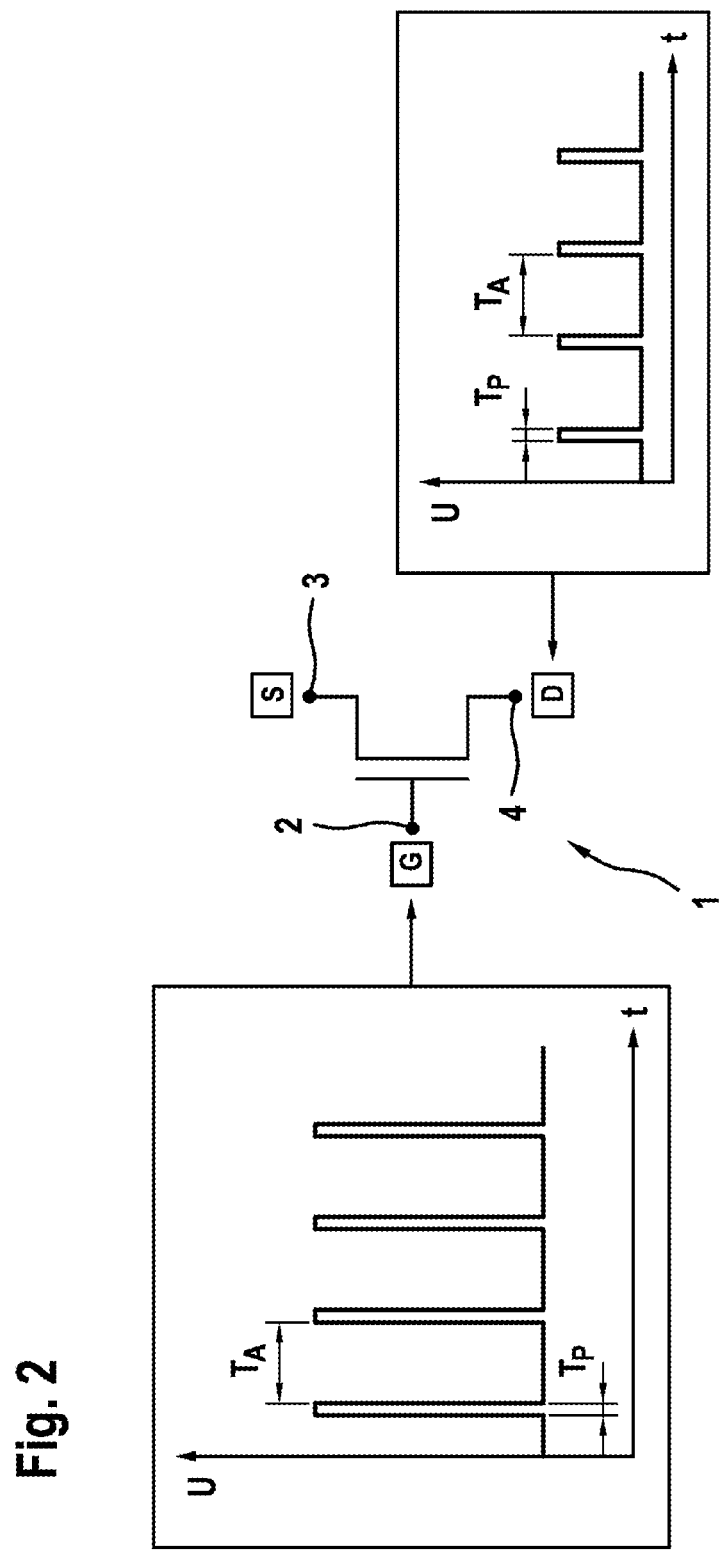

METHOD FOR OPERATING A CHEMICALLY SENSITIVE FIELD-EFFECT TRANSISTOR

This application is a 35 U.S.C. § 371 National Stage Application of PCT/EP2014/070665, filed on Sep. 26, 2014, which claims the benefit of priority to Serial No. DE 10 2013 220 848.0, filed on Oct. 15, 2013 in Germany, the disclosures of which are incorporated herein by reference in their entirety.

BACKGROUND

It is known to use semiconductor devices that are made for example of gallium nitride or silicon carbide for detecting a chemical substance contained in a fluid. Corresponding semiconductor devices may be formed as chemically sensitive field-effect transistors.

The focus of developments so far with respect to such chemically sensitive semiconductor devices has been in particular on their optimum design for detecting a specific chemical substance. In the case of such detection, typically a drift of the offset (known as "baseline drift") is observed. Such an offset drift has various underlying causes with different time constants. These include in particular the generation, charging and discharging of interface states, the redistribution of free charge carriers from trapping sites, the removal of free charge carriers from trapping sites, the generation of defects, the presence of mobile charges in the dielectrics and the changes in the semiconductor, which for weak electrical loads are comparatively small. Altogether, an offset drift has the effect that spontaneously occurring, gas-induced detection signals may only be detectable by observing changes of detection signals, but quantitative measurements are not possible. There are no absolutely measuring gas sensors on the basis of the principle of chemically sensitive field-effect transistors.

SUMMARY

The subject of the disclosure is a method for operating a chemically sensitive field-effect transistor, characterized in that the field-effect transistor is operated by electrical pulses of which the time interval from one another is chosen to be greater than the duration of each individual electrical pulse.

A movement of movable ions present in the chemically sensitive field-effect transistor, which may be induced for example by an ion drift and/or by diffusion, affects the detection signal $I_{ds}$ in particular in the form of an offset drift. Therefore, the movable ions should not change their position within the field-effect transistor during the operation of the field-effect transistor. Furthermore, a degradation of the field-effect transistor brings about an offset drift, which should likewise be prevented.

With the method according to the disclosure, a movement of movable ions within the chemically sensitive field-effect transistor can be avoided to the greatest extent because the electrical pulses of a short time that are used for the measurements only represent a very small disturbance, and therefore a charge distribution present in the chemically sensitive field-effect transistor is only slightly influenced in such a way that the respective distribution of the movable ions can thermally relax during the off times between the electrical pulses, in which no measurements take place. In particular, at the operating temperatures that usually apply, in a range from approximately 100° C. to approximately 700° C., an equilibrium distribution of the movable ions present in a chemically sensitive field-effect transistor is quickly re-established after a disturbance of a short time according to the disclosure. Moreover, by means of the electrical pulses of a short time according to the disclosure or the associated disturbances of a short time, it can be achieved that heavier movable ions do not move at all in the first place, that is to say do not substantially change their respective position during measurements.

The length of time and strength of the electrical pulses and their time interval from one another should be chosen such that no degradation occurs on a chemically sensitive field-effect transistor operated by the method according to the disclosure. Consequently, with the method according to the disclosure, a drift of the offset is avoided to the greatest extent, so that, with a chemically sensitive field-effect transistor operated according to the disclosure, quantitative measurements or detections of at least one chemical substance contained in a fluid are possible over the entire service life of the chemically sensitive field-effect transistor. Moreover, on account of its very low disturbance by measurements, a chemically sensitive field-effect transistor operated by the method according to the disclosure can be operated at various operating points.

The length of time and strength of the electrical pulses and their time intervals from one another are preferably chosen such that the respective signal-to-noise ratio is sufficient and a measurement signal brought about by a gas is at a maximum. Depending on the time duration of an electrical pulse, time windows can be set for the signal evaluation.

Chemically sensitive field-effect transistors can be used for detecting at least one chemical substance in a fluid that is at a temperature in a range from 100° C. to 700° C., preferably from 300° C. to 500° C. The associated application of heat to a chemically sensitive field-effect transistor also has the effect of heating the field-effect transistor. Such heating of the chemically sensitive field-effect transistor is conducive to the mobility of the movable ions contained in the field-effect transistor, which is accompanied by the aforementioned disadvantageous consequences, in particular an offset drift. Therefore, the length of time and the strength of the electrical pulses and their time intervals from one another are preferably chosen such that no movement of movable ions and no degradation occur at the temperatures prevailing during the respective use of the chemically sensitive field-effect transistor.

A chemically sensitive field-effect transistor operated by the method according to the disclosure may be arranged together with a chemically sensitive field-effect transistor operated by another method on a common chip for checking the plausibility of measurement results.

According to an advantageous design, the time interval between the electrical pulses is chosen to be at least one hundred times, preferably at least one thousand times, greater than the duration of each individual electrical pulse. This design has been found to be particularly effective with regard to the quality of achievable measurement results and the optimum suitability for use of a correspondingly operated chemically sensitive field-effect transistor.

According to a further advantageous design, the electrical pulses are at the same level. Alternatively, the levels of the electrical pulses may be varied according to the application.

Advantageously, electrical pulses that directly follow one another in time are at the same time interval from one another. Alternatively, the time intervals between the electrical pulses may be varied according to the application.

It is also regarded as advantageous if the level of each electrical pulse is selected from a range from approximately 100 mV to approximately 10 V. This range has been found to be particularly suitable for carrying out the method.

According to a further advantageous design, electrical pulses are applied to a gate connection and to a drain connection of the field-effect transistor at the same time. This is particularly advisable for carrying out the method. The electrical pulses applied to the gate connection may be at a different level than the electrical pulses applied to the drain connection.

Also the subject of the disclosure is a system for detecting at least one substance contained in a gas, having at least one chemically sensitive field-effect transistor and an electronic evaluation device connected by a communication link to the field-effect transistor, characterized in that the electronic evaluation device is designed for carrying out the method of the disclosure.

Correspondingly associated with this system are the advantages mentioned above with respect to methods.

BRIEF DESCRIPTION OF THE DRAWINGS

The disclosure is explained below by way of example with reference to the appended figures on the basis of preferred exemplary embodiments, the features that are presented below being able both respectively by themselves and in various combinations with one another to represent an aspect of the disclosure. In the figures:

FIG. 1 shows a schematic representation of an exemplary embodiment of a chemically sensitive field-effect transistor operated by the method according to the disclosure in its state of equilibrium and FIG. 2 shows a schematic representation of an activation according to the disclosure of a chemically sensitive field-effect transistor.

DETAILED DESCRIPTION

Figure 1:
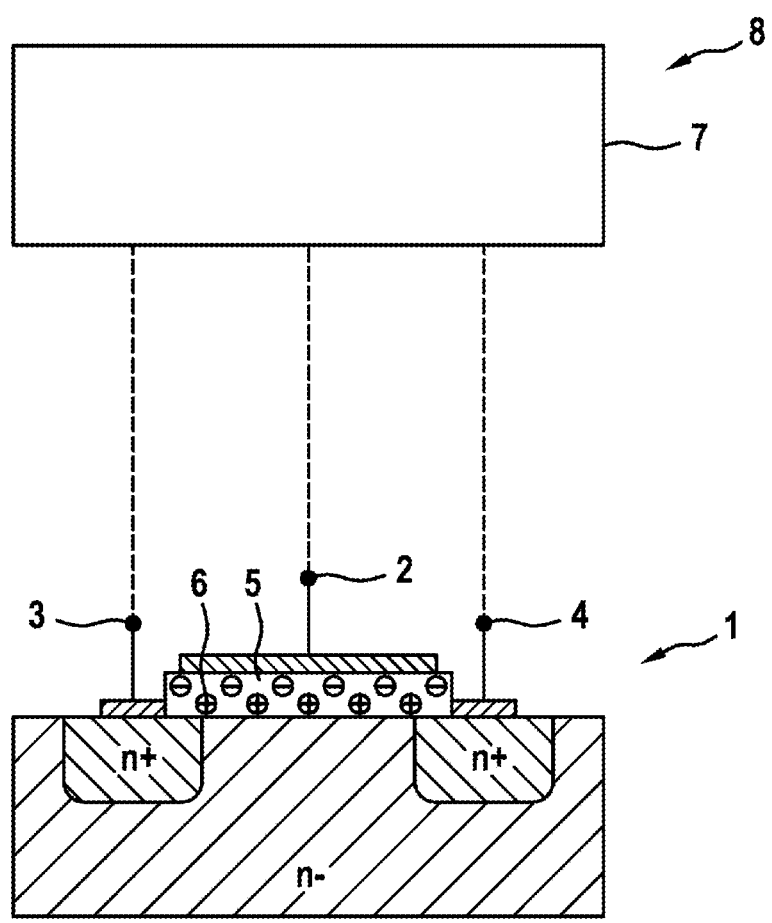

FIG. 1 shows a schematic representation of an exemplary embodiment of a chemically sensitive field-effect transistor 1 operated by the method according to the disclosure in its state of equilibrium. The field-effect transistor 1 of a conventional type has a gate connection 2, a source connection 3 and a drain connection 4. Between the source connection 3 and the drain connection 4 and between the source connection 3 and the gate connection 2 there are no applied electrical voltages. The movable ions 6 present in a gate stack 5 of the chemically sensitive field-effect transistor 1 are uniformly distributed in the gate stack 5. As a result of the minimal disturbance according to the disclosure of this equilibrium distribution of the movable ions 6, the movable ions 6 remain in this equilibrium distribution during virtually the entire service life of the chemically sensitive field-effect transistor 1.

Connected by a communication link to the chemically sensitive field-effect transistor 1 is an electronic evaluation device 7. The chemically sensitive field-effect transistor 1 and the electronic evaluation device 7 form a system 8 for detecting at least one chemical substance.

The electronic evaluation device 7 is designed for operating the chemically sensitive field-effect transistor 1 with electrical pulses of which the time interval $T_A$ from one another is chosen to be greater than the duration $T_P$ of each individual electrical pulse, as indicated by way of example and schematically in FIG. 2. In this case, the time interval $T_A$ between the electrical pulses is chosen to be at least one hundred times, preferably at least one thousand times, greater than the duration $T_P$ of each individual electrical pulse. The electronic evaluation device 8 is designed to apply electrical pulses to the gate connection 2 and to the drain connection 4 of the field-effect transistor 1 at the same time, the level of each electrical pulse being selected from a range from approximately 100 mV to approximately 10 V.

FIG. 2 shows a schematic representation of an activation of a field-effect transistor 1 by means of an exemplary embodiment of a method according to the disclosure. Electrical pulses are applied to the gate connection 2 and to the drain connection 4 at the same time, the electrical pulses applied to the gate connection 1 and to the drain connection 4 being at the same level as one another and the pulse durations $T_P$ and the time intervals $T_A$ between the electrical pulses being chosen to be the same.

The invention claimed is:

1. A method for operating a chemically sensitive field-effect transistor, the method comprising:
   identifying a temperature range of a fluid to be tested; and
   operating the field-effect transistor with electrical pulses, a time interval between each of the electrical pulses being greater than a duration of each of the electrical pulses, wherein an amplitude of each electrical pulse is at least 100 mV and no more than 10 V, wherein the time interval between each of the electrical pulses, the duration of each of the electrical pulses, and the amplitude of each electrical pulse is selected based upon the identified temperature range such that no movement of movable ions present in a gate stack of the chemically sensitive field-effect transistor occurs during operation of the chemically sensitive field-effect transistor in the identified temperature range.

2. The method as claimed in claim 1, wherein the time interval between each of the electrical pulses is at least one hundred times greater than the duration of each of the electrical pulses.

3. The method as claimed in claim 1, wherein the electrical pulses each have an equal amplitude to one another.

4. The method as claimed in claim 1, wherein the time interval between each of the electrical pulses is equal between each of the electrical pulses.

5. The method as claimed in claim 1, wherein electrical pulses are applied to a gate connection of the field-effect transistor and to a drain connection of the field-effect transistor concurrently.

6. The method as claimed in claim 1, wherein the time interval between each of the electrical pulses is at least one thousand times greater than the duration of each of the electrical pulses.

7. A system for detecting at least one substance contained in a gas, the system comprising:
   at least one chemically sensitive field-effect transistor; and
   an electronic evaluation device connected by a communication link to the field-effect transistor, the electronic evaluation device configured to operate the field-effect transistor with electrical pulses, a time interval between each of the electrical pulses greater than a duration of each of the electrical pulses, wherein an amplitude of each electrical pulse is at least 100 mV and no more than 10 V, wherein the electrical pulses, the time interval, and the amplitude are selected based upon an identified temperature range of a fluid to be tested such that no movement of movable ions present in a gate stack of the at least one chemically sensitive field-effect transistor occurs during operation of the at least one chemically sensitive field-effect transistor in the identified temperature range.

* * * * *